United States Patent [19]

Ayer et al.

[11] Patent Number: 5,030,456
[45] Date of Patent: Jul. 9, 1991

[54] DOSAGE FORM FOR TREATING CARDIOVASCULAR DISEASES

[75] Inventors: Atul D. Ayer; David R. Swanson; Anthony L. Kuczynski, all of Palo Alto, Calif.

[73] Assignee: ALZA Corporation, Palo Alto, Calif.

[21] Appl. No.: 516,582

[22] Filed: Apr. 30, 1990

Related U.S. Application Data

[63] Continuation of Ser. No. 267,904, Nov. 7, 1988, Pat. No. 4,950,486.

[51] Int. Cl.[5] .................................. A61K 9/34
[52] U.S. Cl. ..................................... 424/473; 424/468
[58] Field of Search ............................ 424/473, 468

[56] References Cited

U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,063,064 | 12/1977 | Saunder et al. | 219/121 L |
| 4,088,864 | 5/1978 | Theeuwes et al. | 219/121 LM |
| 4,200,098 | 4/1980 | Ayer et al. | 128/260 |
| 4,285,987 | 8/1981 | Ayer et al. | 427/3 |
| 4,327,725 | 5/1982 | Cortese et al. | 128/260 |
| 4,612,008 | 9/1986 | Wong et al. | 604/892 |
| 4,723,957 | 2/1988 | Magruder et al. | 424/78 |
| 4,764,378 | 8/1988 | Keith et al. | 424/78 |
| 4,867,969 | 9/1989 | Magruder et al. | 424/78 |
| 4,873,086 | 10/1989 | Good et al. | 424/78 |

OTHER PUBLICATIONS

Greenberg, MD, Barry et all., The Amer. Jol. of Cardiology, vol 59, Jan. 30, 1987, pp. 70B–74B, "Hemodynamic Effects of PN 200–100 (Isradipine) in Congestive Heart Failure."

Primary Examiner—Thurman K. Page
Assistant Examiner—Leon R. Horne
Attorney, Agent, or Firm—Paul L. Sabatine; Edward L. Mandell; Steven F. Stone

[57] ABSTRACT

An osmotic device is disclosed comprising a first composition, and a second composition with the beneficial drug isradipine in the first composition.

1 Claim, 1 Drawing Sheet

DOSAGE FORM FOR TREATING CARDIOVASCULAR DISEASES

This is a continuation of U.S. application Ser. No. 07/267,904, filed on Nov. 7, 1988, now U.S. Pat. No. 4,950,486.

FIELD OF THE INVENTION

This invention pertains to a dosage form comprising the beneficial drug isradipine useful for treating cardiovascular diseases.

BACKGROUND OF THE INVENTION

A considerable need exists for a dosage form useful for treating cardiovascular diseases. The dosage form should be therapeutically indicated for treating cardiovascular diseases including angina pectoris, hypertension, congestive heart failure, and possess vasodilation properties for decreasing systematic vascular resistance.

The beneficial drug isradipine is therapeutically indicated for treating cardiovascular diseases. The cardiovascular diseases include angina, pectoris, hypertension and congestive heart failure as disclosed in a patient study reported in *The American Journal of Cardiology*, Vol. 59, pp 70B-74B, (1987). The drug was administered in the study in a bulk, nonrate uncontrolled dose that was subjected to the changing adverse environment of the gastrointestinal tract.

In light of the above presentation it will be appreciated by those versed in the dispensing art to which this invention pertains that a pressing need exists for a rate controlled dosage form that can deliver the valuable drug isradipine to a patient in critical need of cardiovascular therapy. The pressing need exists also for an oral dosage form that can deliver isradipine at a controlled rate in a constant dose per unit time over a prolonged period of time for its beneficial hemodynamic effects substantially independent of the variable environment of the gastrointestinal tract. It will be appreciated further by those versed in the dispensing art that such a novel and unique dosage form that can administer isradipine in a rate controlled dose over time, and simultaneously provide cardiovascular therapy, would represent an advancement and valuable contribution to the art.

OBJECTS OF THE INVENTION

Accordingly, in view of the above presentation, it is an immediate object of this invention to provide a dosage form for delivering isradipine in a rate controlled amount, and which dosage form substantially overcomes the deficiencies associated with the prior art.

Another object of the present invention is to provide a dosage form for administering isradipine in a rate controlled dose over a prolonged period of time for cardiovascular therapy.

Another object of the invention is to provide a pharmaceutical dosage form that makes available sustained and controlled isradipine therapeutic activity.

Another object of the invention is to provide a novel dosage form manufactured as an osmotic device that can administer isradipine to a biological receptor site to produce the desired pharmaceutical effects.

Another object of the present invention is to provide dosage form manufactured as an osmotic dosage form that substantially reduces and/or substantially eliminates the unwanted influences of the gastrointestinal environment of use and still provides controlled administration of isradipine over time.

Another object of the present invention is to provide a dosage form adapted for oral administration of isradipine, which dosage form comprises a first composition and a contacting second composition that act in harmony for the rate controlled administration of isradipine over time.

Another object of the present invention is to provide a complete pharmaceutical regimen comprising a composition comprising isradipine that can be dispensed from a drug delivery device, the use of which requires intervention only for initiation and possibly for termination of the regimen.

Another object of the invention is to provide a method of treating cardiovascular diseases by orally administering isradipine in a rate controlled dosage per unit time to a warm-blooded animal in need of cardiovascular therapy Other objects, features and advantages of the invention will be more apparent to those versed in the dispensing arts from the following detailed specification, taken in conjunction with the drawings and the accompanying claims.

BRIEF DESCRIPTION OF THE DRAWINGS

In the drawing figures, which are not drawn to scale but are set forth to illustrate various embodiments of the invention, the drawing figures are as follows.

DETAILED DESCRIPTION OF THE DRAWINGS

Figure 1:
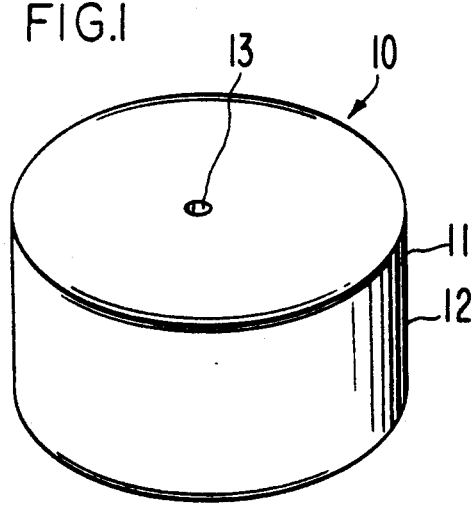
FIG. 1 is a view of a dosage form designed and shaped for orally administering isradipine to gastrointestinal isradipine receptors of a warm-blooded animal.

Turning now to the drawing figures in detail, which drawing figures are an example of the dosage form provided by this invention and which example is not to be construed as limiting, one example of the dosage form is illustrated in FIG. 1 and designated by the numeral 10. In FIG. 1 dosage form 10 comprises a body member 11 comprising a wall 12 that surrounds and encloses an internal compartment, not seen in FIG. 1. Dosage form 10 comprises at least one exit means 13 for connecting the interior of dosage form 10 with the exterior environment of use.

Figure 2:
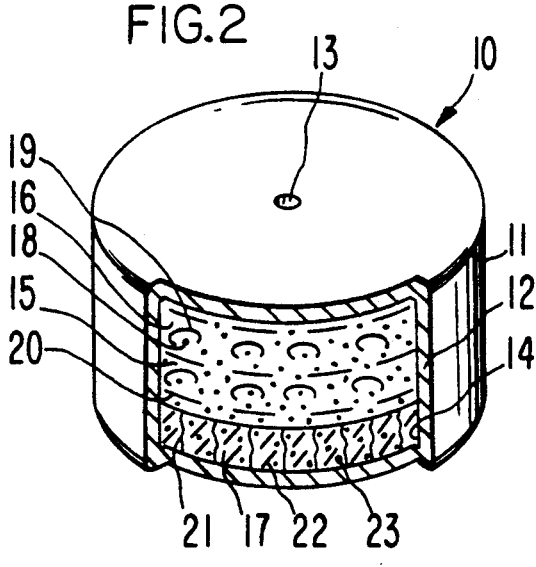
FIG. 2 is an opened view of the dosage form of FIG. 1 illustrating the internal structure of the dosage form.

In FIG. 2 dosage form 10, manufactured as an osmotic device, is seen in opened view. In FIG. 2, dosage form 10 comprises body 11, wall 12, that is sectioned at 14, and which wall 12 surrounds and defines an internal compartment 15. Wall 12 comprises at least one exit means 13 that connects compartment 15 with the exterior of dosage form 10. Dosage form 10 can comprise more than one exit means 13.

Wall 12 of dosage form 10 comprises in at least a part a composition that is permeable to the passage of an exterior fluid present in the environment of use and it is substantially impermeable to the passage of isradipine and other ingredients present in compartment 15. The composition is semipermeable, it is substantially inert, and it maintains its physical and chemical integrity during the dispensing life of isradipine from dosage form 10. The phrase, "keeps its physical and chemical integrity" means wall 12 does not lose its structure and it does not change during the dispensing life of dosage form 10. Wall 12 comprises at least in part from 70 weight percent to 100 weight percent of a cellulosic polymer. The cellulosic polymer comprises a member selected from the group consisting of cellulose acylate, cellulose diacylate, cellulose triacylate, cellulose acetate, cellulose diacetate and cellulose triacetate. In another embodiment wall 12 can comprise additionally from 0 weight percent to 30 weight percent of a member selected from the group consisting of a cellulose ether selected from the group consisting of hydroxypropylcellulose and hydroxypropylmethylcellulose, and from 0 weight percent to 20 weight percent polyethylene glycol. The total amount of all components comprising wall 12 is equal to 100 weight percent Internal compartment 15 comprises a first lamina 16, which also can be defined optionally as a first composition 16, and a second lamina 17, which also can be defined optionally as a second composition 17. First lamina 16 and second lamina 17 initially are in laminar arrangement and they cooperate with each other and dosage form 10 for the effective delivery of isradipine from dosage form 10.

First composition 16 comprises from 2 weight percent to 30 weight percent of the therapeutically beneficial drug isradipine identified by dots 18; from 30 weight percent to 95 weight percent of a polyethylene oxide, identified by bowed lines 19; which polyethylene oxide in one embodiment is a member selected from a polyethylene oxide having a molecular weight of about 100,000; a polyethylene oxide having a molecular weight of about 200,000 and a polyethylene oxide having a molecular weight of about 300,000; and from 0 weight percent to 15 weight percent of a hydroxypropylmethylcellulose, identified by dashes 20, having a number average molecular weight of about 9,000 to 15,000, with the total weight percent of all ingredients equal to 100 weight percent. The first composition optionally can comprise from zero weight percent to 3 weight percent of a lubricant, such as zero weight percent to 3 weight percent of magnesium stearate.

First composition 16 in another embodiment comprises 2 weight percent to 30 weight percent of isradipine; from 30 weight percent to 40 weight percent of polyethylene oxide having a molecular weight of 200,000; from 45 weight percent to 55 weight percent of a polyethylene oxide having a molecular weight of about 300,000; from zero weight percent to 15 weight percent of a hydroxypropylmethylcellulose having an number average molecular weight of about 9,000 to 15,000, with the total weight percent of all ingredients equal to 100 weight percent. The first composition optionally can comprise from 0.10 weight percent to 2.0 weight percent of a lubricant.

Second composition 17 comprises from 55 weight percent to 70 weight percent of a polyethylene oxide, identified by vertical wavy lines 21, having having an average molecular weight of about 5,000,000 to 7,800,000, from 15 weight percent to 30 weight percent of an osmotically effective solute identified by slanted lines 22; and from 5 weight percent to 15 weight percent of a hydroxypropylmethylcellulose, identified by dots 23, and having a number average molecular weight of 9,000 to 20,000. The second composition optionally comprises from 0.10 to 3.0 weight percent of a lubricant and from 0.20 weight percent to 2.0 weight percent of ferric oxide, with the total weight percent of all ingredients equal to 100 weight percent.

In the second composition 17, the polyethylene oxide comprising a molecular weight of about 7,000,000 to 7,800,000 exhibits a viscosity range at 25° C. from 7,500 to 10,000 centipoises, cps, of a 1% solution. The presence of the polyethylene oxide with the high molecular weight and its accompanying high viscosity provide unexpected advantages for the dosage form. For example, the high viscosity polymer remains in the second composition substantially free of migration into the first composition. The presence of the high viscosity polyethylene oxide in the second composition increases the operating efficiency of the dosage form as the simultaneous hydration and swelling of the polymer are maintained at a higher level over a prolonged period of time. These combined properties enable the second composition to push the first composition at a more constant and uniform rate over the prolonged period of time. The constant pushing against the first composition assures a uniform rate of release of isradipine from the dosage form and concomitantly substantially prevents a declining and decreasing release rate of drug over time. The polyethylene oxide comprising a molecular weight of 7,000,000 to 7,800,000 is commercially available from the Union Carbide Corporation, South Charleston, W. Va.

The expression, "exit means" 13, as used herein, comprises means and methods suitable for the metered release of beneficial drug isradipine from compartment 15 of dosage form 10. The means 13 includes at least one passageway, orifice, or the like, through wall 12 for communicating with isradipine in compartment 15. The expression, porous element through which the drug can migrate, hollow fiber, capillary tube, porous overlay, porous insert, and the like. The expression also includes a material that erodes or is leached from wall 12 in the fluid environment of use to produce at least one passageway in dosage form 10. Representative material suitable for forming at least one passageway, or a multiplicity of passageways, include an erodible poly(-glycolic) acid or poly(lactic) acid member in the wall; a gelatinous filament; poly(vinyl alcohol); leachable materials such as fluid removable pore forming polysaccharides, salts, or oxides, and the like. A passageway or a plurality of passageways can be formed by leaching a material such as sorbitol from the wall. The passageway can have any shape such as round, triangular, square, elliptical, and the like, for assisting in the metered release of isradipine from dosage form 10. Dosage form 10 can be constructed with one or more passageways in spaced apart relations or more than a single surface of a dosage form.

Passageway and equipment for forming passageways are disclosed in U.S. Pat. Nos. 3,845,770; 3,916,899; 4,063,064 and 4,088,864. Passageways formed by leaching are disclosed in U.S. Pat. Nos. 4,200,098 and 4,285,987.

The osmotic device of the invention is manufactured by standard techniques. For example, in one embodiment the beneficial drug isradipine is mixed with the osmopolymer and pressed into a solid lamina possessing dimensions that correspond to the internal dimensions of the compartment space adjacent to a passageway. In another embodiment the beneficial drug isradipine and other first composition forming ingredients and a solvent are mixed into a solid, or a semisolid, by conventional methods such as ballmilling, calendering, stirring or rollmilling, and then pressed into a preselected lamina forming shape Next, a lamina of a composition comprising an osmopolymer and an osmoagent are placed in contact with the lamina comprising the beneficial drug, and the two lamina comprising the laminate are surrounded with a semipermeable wall. The lamination of the first beneficial drug composition and the second osmopolymer osmagent composition can be accomplished by using a conventional two-layer tablet press technique. The wall can be applied by molding, spraying or dipping the pressed shapes into wall forming materials. Another and presently preferred technique that can be used for applying the wall is the air suspension coating procedure. This procedure consists in suspending and tumbling the two layered laminate in current of air until the wall forming composition surrounds the laminate. The air suspension procedure is described in U.S. Pat. No. 2,799,241; *J. Am. Pharm. Assoc.*, Vol. 48, pp 451-459 (1979); and, *ibid*, Vol. 49, pp 82-84 (1960). Other standard manufacturing procedures are described in *Modern Plastics Encyclopedia*, Vol. 46, pp 62-70 (1969); and in *Pharmaceutical Science*, by Remington, 14th Ed., pp 1626-1978, (1970), published by Mack Publishing Co., Easton, Pa.

Exemplary solvents suitable for manufacturing the wall, the laminates and laminae include inert inorganic and organic solvents that do not adversely harm the materials and the final wall or the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monoethyl acetate, methylene dichloride, ethylene dichloride, propylene dichloride, carbon tetrachloride, chloroform, nitroethane, nitropropane, tetrachloroethane, ethyl ether, isopropyl ether, cyclohexane, cyclo-octane, benzene, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DESCRIPTION OF EXAMPLES

The following examples are merely illustrative of the present invention and they should not be considered as limiting the scope of the invention in any way as these examples and other equivalents thereof will become apparent to those versed in the art in the light of the present disclosure, the drawings and the accompanying claims.

EXAMPLE 1

A dosage form adapted, designed and shaped as an osmotic drug delivery system is manufactured as follows: first, the drug containing composition is prepared by passing through a 40 mesh screen 53.5 g of polyethylene oxide having a molecular weight of about 200,000. Then 15 g of isradipine and 30 g of hydroxypropylmethylcellulose having a number average molecular weight of 11,200 is added to the polyethylene oxide and the three ingredients mixed for about 10 minutes in a conventional mixer While the three ingredients are mixing, 300 ml of denatured, anhydrous ethanol is slowly added to the mixer and the mixing continued for an additional five minutes The wet granulation is passed through a 20 mesh screen, dried at room temperature for 16 hours and passed again through the 20 mesh screen. Finally, 1.5 g of magnesium stearate is added to the granulation and all the ingredients mixed in a rollermill for 1 to 3 minutes.

The second composition is prepared by mixing 194.5 g of polyethylene oxide having a molecular weight of 7,500,000 with 72 g of sodium chloride and the homogeneous blend passed through a 40 mesh screen. Then, the just prepared mixture is mixed with 30 g of hydroxypropylmethylcellulose having a number average molecular weight of 11,200 and with 3 g of ferric oxide for 10 minutes in a mixer. Then, 300 ml of denatured, anhydrous ethanol is slowly added to the blending mixture and all the ingredients mixed for an additional 5 minutes. The freshly prepared wet granulation is passed through a 20 mesh screen, allowed to dry at room temperature for 16 hours, and again passed through a 20 mesh screen. The screened granulation is mixed with 1.5 g of magnesium stearate in a rollermill for 1 minute.

A three-layered press is used for forming the laminate. First, 220 mg of the first composition comprising the drug is added to the press and tamped; then, 130 mg of the second lamina forming composition is added to the press and the two laminae pressed into a contacting laminated arrangement.

Next, the laminate is surrounded with a semipermeable wall. The wall forming composition comprises 97% cellulose acetate having an acetyl content of 39.8% and 3% polyethylene glycol having a molecular weight of 3350. The wall forming composition is dissolved in methylene chloride:methanol (90:10 wt:wt) solvent to make a 4% solids solution. The wall forming composition is sprayed onto and around the bilaminate in an Aeromatic Air ® Suspension Coater.

Finally the wall coated bilaminates are dried for 24 hours at room temperature. Then, a 25 mil (0.635 mm) exit orifice is laser drilled on the drug laminate side of the osmotic device. The residual solvent is removed by drying the osmotic system for 48 hours at 50° C. and 50% relative humidity. The osmotic systems are then dried for one hour at 50° C. to remove the excess moisture.

EXAMPLE 2

Figure 3:
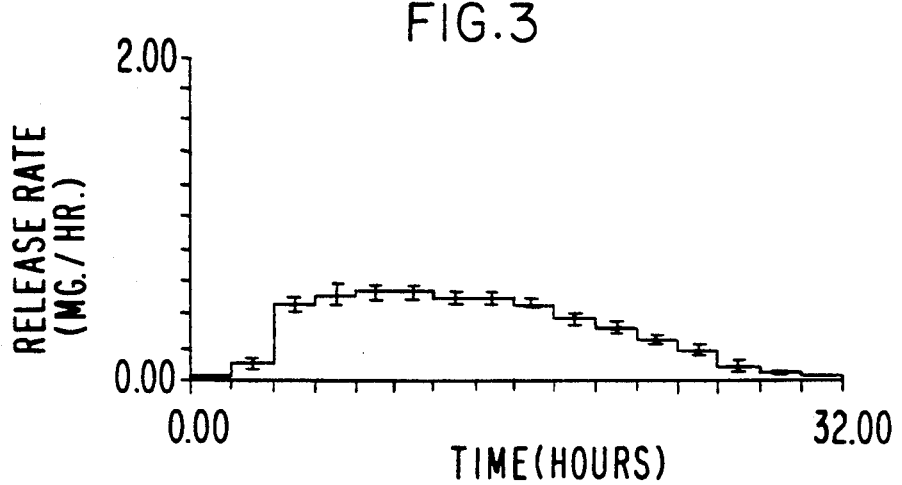
FIG. 3 is a graph depicting the dose amount of isradipine released per hour over a prolonged period of time from a dosage form; and, FIG. 4 is a graph depicting the cumulative amount of isradipine delivered by a dosage form over a prolonged period of time up to 32 hours In the drawing figures and in the specification like parts in related drawing figures are identified by like numbers. The terms appearing earlier in the specification and in the description of the drawings, as well as embodiments thereof, are further described elsewhere in the disclosure.
Figure 4:
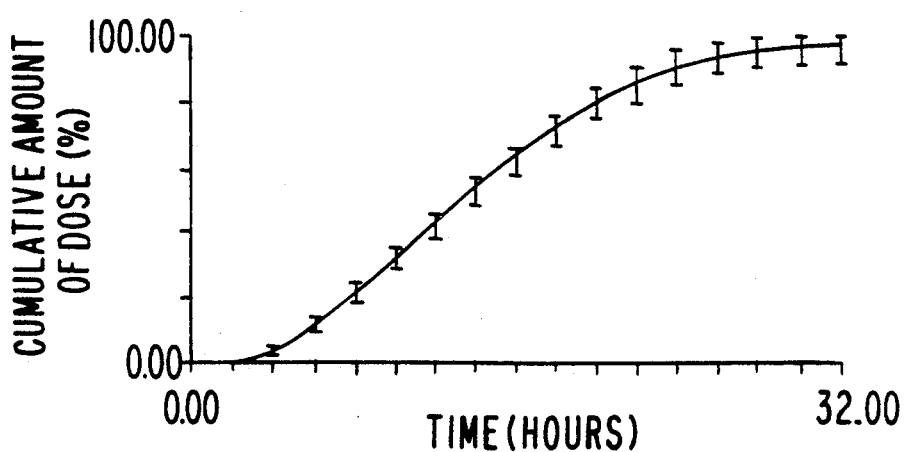

Following the procedure of Example 1, an osmotic device is manufactured comprising a first composition comprising 5 weight percent isradipine; 84.75 polyethylene oxide having a molecular weight of 200,000, 10 weight percent hydroxypropylmethylcellulose having a number average molecular weight of 11,200; and 0.25 weight percent magnesium stearate; a second composition comprising 64.75 weight percent polyethylene oxide having a molecular weight of 7,500,000; 24 weight percent sodium chloride; 10 weight percent hydroxypropylmethylcellulose having a number average molecular weight of 11,200, 1 weight percent ferric oxide and 0.25 weight percent magnesium stearate; and a semipermeable wall comprising 97 weight percent cellulose acetate having an acetyl content of 39.8%; and 3 weight percent polyethylene glycol having a molecular weight of 4000. The device comprises a 25 mil exit orifice, contains 11 mg of isradipine and a mean release rate of 0.505 mg/hr of isradipine. Accompanying FIG. 3 depicts the release rate over time and FIG. 4 depicts the cumulative amount release over a prolonged period of time.

EXAMPLE 3

The procedure of example 1 is repeated with the manufacturing steps as previously described, except that sodium chloride is replaced by an osmotically effective solute selected from the group consisting of potassium chloride, magnesium chloride, d-mannitol and lactose monohydrate.

EXAMPLES 4 TO 8

A series of osmotic dosage forms are manufactured by following the above procedures for providing osmotic dosage forms that release from 0.1 mg/hr to 1.0 mg/hr of isradipine The dosage forms are as follows: (a) a dosage form comprising a first lamina comprising 2.20 2.20 mg (2.5 wt %) of isradipine, 76.78 mg (87,25 wt %) of polyethylene oxide having a 200,000 molecular weight, 8.80 mg (10.00 wt %) hydroxypropylmethylcellulose having a 11,200 number average molecular weight, and 0.22 mg (0.25 wt %) magnesium stearate and a second lamina comprising 33.67 mg (64.75 wt %) of polyethylene oxide having a 7,200,000 molecular weight, 12.48 mg (24 wt %) sodium chloride, 5.2 mg (10 wt %) hydroxypropylmethylcellulose having a 11,200 number average molecular weight, 0.52 mg (1 wt %) of ferric oxide and 0.13 mg (0.25 wt %) of magnesium stearate, a wall comprising 97 wt % cellulose acetate having a 39.8% acetyl content, 3 wt % polyethylene glycol 3350, a single passageway and a delivery rate of 0.1 mg/hr of isradipine for 18 hours or longer; (b) a dosage form comprising a first composition which composition comprises 5.5 mg (5 wt %) of isradipine, 93.225 mg (84.75 wt %) of polyethylene oxide having a 200,000 molecular weight, 11 mg (10 wt %) of hydroxypropylmethylcellulose having 11,200 number average molecular weight, 0.275 mg (0.25 wt %) of magnesium stearate, a second composition comprising 42.08 mg (64.75 wt %) of polyethylene oxide having a 7,200,000 molecular weight, 15.60 mg (24 wt %) of sodium chloride, 6.5 mg (10 wt %) of hydroxypropylmethylcellulose having a 11,200 number average molecular weight., 0.65 mg (1 wt %) of ferric oxide and 0.162 mg (0.25 Wt %) of magnesium stearate, a wall comprising 97 wt % cellulose acetate having a 39.8 % acetyl content, 3 wt % polyethylene glycol 3350, a single passageway and a delivery rate of 0.30 mg/hr of isradipine for 18 hours or longer; (c) a dosage form comprising a first lamina comprising 11 mg (5 wt %) of isradipine, 186.45 mg (84.75 wt %) of polyethylene oxide having a 200,000 molecular weight, 22 mg (10 wt %) of hydroxypropylmethylcellulose having a 11,200 number average molecular weight, 0.55 mg (0.25 wt %) of magnesium stearate, a second lamina comprising 84.175 mg (64.75 wt %) of polyethylene oxide having a 7,200,000 molecular weight, 31.20 mg (24 wt %) sodium chloride, 13 mg (10 wt %) hydroxypropylmethylcellulose having a 11,200 number average molecular weight, 1.3 mg (1 wt %) ferric oxide, 0.325 mg (0.25 wt %) magnesium stearate, a wall comprising 97 wt % cellulose acetate having a 39.8% acetyl content and 3 wt % polyethylene glycol 3350, a single passageway, and a delivery rate of 0.75 mg/hr of isradipine for 12 hours or longer; (d) a dosage form comprising a first lamina comprising 16.5 mg (7.5 wt %) of isradipine, 186.45 mg (84.75 wt %) of polyethylene oxide having a 200,000 molecular weight, 16.50 mg (7.5 wt %) of hydroxypropylmethylcellulose having a 11,200 number average molecular weight, and 0.55 mg (0.25 wt %) magnesium stearate, a second lamina comprising 84.175 mg (64.75 wt %) of polyethylene oxide having a 7,200,000 molecular weight, 31.20 mg (24 wt %) of sodium chloride, 13 mg (10 wt %) of hydroxypropylmethylcellulose having a 11,200 number average molecular weight, 1.3 mg (1 wt %) ferric oxide, and 0.325 mg (0.25 wt %) magnesium stearate, a wall comprising 97 wt % cellulose acetate having a 39.8% acetyl content and 3 wt % polyethylene glycol 3350, a single passageway, and a delivery rate of 0.75 mg/hr over a prolonged period of 22 hours or longer; (e) an osmotic dosage form comprising a first lamina comprising 22 mg (10 wt %) isradipine, 186.56 mg (84.75 wt %) of polyethylene oxide having a 200,000 molecular weight, 11 mg (5.00 wt %) of hydroxypropylmethylcellulose having a 11,200 number average molecular weight, and 0.55 mg (0.25 wt %) of magnesium stearate, a second lamina comprising 84.175 mg (64.75 wt %) of polyethylene oxide having a 7,200,000 molecular weight, 31.2 mg (24 wt %) of sodium chloride, 13 mg (10 wt %) of hydroxypropylmethylcellulose having a 11,200 number average molecular weight, 1.3 mg (1 wt %) of ferric oxide, and 0.325 mg (0.25 wt %) of magnesium stearate, and a wall comprising 97 wt % cellulose acetate having a 39.8% acetyl content and 3 wt % polyethylene glycol 3350, which dosage form comprises a single passageway and delivers 1.0 mg/hr of isradipine over a 20 hour period or longer.

EXAMPLES 9 AND 10

An osmotic dosage form is prepared by following the above examples. In this example the dosage form (f) comprises a first composition comprising 22 mg (10 wt %) isradipine, 76.45 mg (34.75 wt %) of polyethylene oxide having a 300,000 molecular weight, 110 mg (50 wt %) polyethylene oxide having a 200,000 molecular weight, 11 mg (5 wt %) hydroxypropylmethylcellulose having a 11,200 number average molecular weight, and 0.55 mg (0.25 wt %) magnesium stearate, a second composition comprising 84.175 mg (64 75 wt %) polyethylene oxide having a 7,200,000 molecular weight, 31.2 mg (24 wt %) sodium chloride, 13 mg (10 wt %) hydroxypropylmethylcellulose having a 11,200 number average molecular weight, 1.3 mg (1 wt %) ferric oxide, and 0:325 mg (0.25 wt %) magnesium stearate, a wall comprising 97 wt % cellulose acetate having a 39.8% acetyl content and 3 wt % polyethylene glycol 3350, and a single passageway; and (g) an osmotic dosage form comprising a first composition comprising 16.5 mg (7.5 wt %) of isradipine, 66 mg (30 wt %) of polyethylene oxide having a 300,000 molecular weight, 120.45 mg (54.75 wt %) of polyethylene oxide having a 200,000 molecular weight, 11 mg (5 wt %) hydroxypropylmethylcellulose having a 11,200 number average molecular weight, and 0.55 mg (0.25 wt %) magnesium stearate, a second composition comprising 84.175 mg (64.75 wt %) polyethylene oxide having a 7,200,000 molecular weight, 31.2 mg (24 wt %) sodium chloride, 13 mg (10 wt %) hydroxypropylmethylcellulose having a 11,200 number average molecular weight. 1.3 mg (1 wt %) ferric oxide, and 0.325 mg (0 25 wt %) magnesium stearate, a wall comprising 97 wt % cellulose acetate having a 39.8% acetyl content and 3 wt % polyethylene glycol 3350, and an osmotic passageway.

EXAMPLE 11

The procedure of the above examples are followed for providing a dosage form with all conditions as set forth, except that in this example the first composition comprises from 2 mg to 20 mg of isradipine, and the wall comprises 90 wt % cellulose acetate having a 39.8% acetyl content, 7 wt % cellulose acetate having a 32% acetyl content, and 3 wt % polyethylene glycol having a 3350 molecular weight.

In summary, it will be appreciated that the present invention contributes to the art an unobvious dosage form that possesses practical utility, can administer isradipine at a dose metered-release-rate per unit time While the invention has been described and pointed out in detail with reference to operative embodiments thereof, it will be understood that those skilled in the art will appreciate that various changes, modifications, substitutions and omissions can be made without departing from the spirit of the invention It is intended, therefore, that the invention embrace those equivalents within the scope of the claims which follow.

We claim:

1. A composition for use in an osmotic device, said composition comprising a polyethylene oxide comprising a molecular weight of about 7,000,000 to 7,800,000 and an osmotically effective compound, and which composition when in use in an osmotic device is means for delivering a drug from the osmotic device over a prolonged period of time.

* * * * *